United States Patent
Tuffet et al.

(10) Patent No.: US 6,461,571 B1
(45) Date of Patent: Oct. 8, 2002

(54) METHOD FOR PROLONGED STORAGE OF DNA MOLECULES AND PACKAGING IMPLEMENTING SAID METHOD

(76) Inventors: Sophie Tuffet, 15 rue de Cadaujac F-33800, Bordeaux (FR); David Georges De Souza, 15 rue de Cadaujac F-33800, Bordeaux (FR); Joseph Portier, 9 rue de Gazaillan F-33710, Gradignan (FR); Jacques Bonnet, 3 allée Albert Camus F-33600, Pessac (FR); Guy Campet, 5 place de l'Estandit F-33610, Canejan (FR); Thierry Noel, 24 rue de Cérons F-33800, Bordeaux (FR)

( * ) Notice: Subject to any disclaimer, the term of this patent is extended or adjusted under 35 U.S.C. 154(b) by 0 days.

(21) Appl. No.: 09/674,704

(22) PCT Filed: May 6, 1998

(86) PCT No.: PCT/FR98/00912

§ 371 (c)(1), (2), (4) Date: Nov. 6, 2000

(87) PCT Pub. No.: WO99/57264

PCT Pub. Date: Nov. 11, 1999

(51) Int. Cl.⁷ .................. G01N 15/06; G01N 33/00; G01N 33/48; C07H 19/00
(52) U.S. Cl. .................. 422/68.1; 422/243; 536/22.1
(58) Field of Search .................. 536/22.1; 422/68.1, 422/243

(56) References Cited

U.S. PATENT DOCUMENTS 5,565,318 A * 10/1996 Walker et al. .................. 435/4

* cited by examiner

*Primary Examiner*—Jezia Riley
(74) *Attorney, Agent, or Firm*—Young & Thompson

(57) ABSTRACT

A process for the long-term preservation of DNA molecules and a packaging for practicing the same provides for extraction, purification and dehumidification of the DNA by any suitable technique carrying out an encapsulation in a sealed corrosion-proof metallic capsule of the DNA molecule.

13 Claims, 1 Drawing Sheet

METHOD FOR PROLONGED STORAGE OF DNA MOLECULES AND PACKAGING IMPLEMENTING SAID METHOD

BACKGROUND OF THE INVENTION

The present invention relates to DNA (desoxyribonucleic acid) particularly of human origin, and seeks to preserve the DNA molecule, which carries the genes characteristic of each individual, which is to say his genetic inheritance.

More precisely, the invention seeks to safeguard the genetic information by the preservation of the DNA molecule so as to prolong as long as possible and under conditions which preserve the integrity of the genetic information. This invention has numerous interests, particularly for predictive medicine, for genetic genealogy and identification.

DESCRIPTION OF THE RELATED ART

If the DNA molecule is relatively stable, archeogenetic studies have shown that it can be preserved for millions of years in a favorable environment, but that it can be degraded in the absence of preservation in such an environment.

Among the causes of alteration of the DNA, can be cited the action of ionizing radiation such as x-rays or gamma rays, the action of ultraviolet radiation, oxidation and enzymatic or chemical hydrolysis.

SUMMARY OF THE INVENTION

The present invention seeks to provide a technique for the preservation of DNA in an environment preserving it from the effects of the above actions.

To this end, the invention has for its object a process for the long-term preservation of DNA molecules, characterized in that it consists, after extraction and purification of the DNA by any suitable technique, conventional and not, in carrying out an encapsulation in a sealed corrosion-proof metallic capsule, of the preliminary dehumidified DNA molecule.

According to a first embodiment of the process, the DNA is encapsulated in an atmosphere constituted by one or several inert gases and having a degree of humidity less than or equal to 1 ppm of water.

According to a second embodiment of the process, before said physical encapsulation, the DNA is subjected to a chemical encapsulation by cladding in a suitable (co) polymer.

According to a modification of this second embodiment, the chemical encapsulation is carried out with a hybrid constituted of said (co)polymer, of organic molecules and/or inorganic salts, for enhanced protection of the DNA as to ultraviolet or ionizing radiations.

Preferably, and no matter what the embodiment of the process, the physical encapsulation is completed by placing said sealed and corrosion-proof metallic capsule in a container resistant to shock and crushing.

The thus-encapsulated DNA can theoretically be preserved for several tens of thousands of years, sheltered from ionizing radiations, ultraviolet radiations, chemical aggression and mechanical stress.

The invention also has for its object the different types of packaging obtained according to the process, which are present in the form either of a single capsule, or a capsule enclosed in a protective envelope called a container.

DESCRIPTION OF THE PREFERRED EMBODIMENTS

Within the capsule is preserved a quantity of DNA, for example 30 μg, sufficient to carry out a substantial number of sample withdrawals at any time.

The DNA is disposed directly on the capsule, or on a glass dish introduced into the capsule.

Upon taking each specimen, the capsule is opened, the desired quantity of DNA is removed, the rest being left in the capsule, the sealed packaging being reconstituted. The removed DNA is then rehydrated for analytical purposes.

Such a package ensures perpetual preservation of the genetic inheritance which is protected particularly from oxidation and ionizing ultraviolet radiations as well as other chemical or mechanical attacks.

Other characteristics and advantages will become apparent from the description which follows, of embodiments of the process according to the invention, which description is given solely by way of example and with respect to the accompanying drawing, in which the single figure schematically shows a structure of a packaging according to the invention.

Prior to practice of the invention, the DNA is extracted and purified.

This can be carried out by any conventional method or not. The DNA can be extracted from no matter what cells of the organism.

By way of example, the DNA is extracted from blood or hair follicles, of cells from saliva, from the mucosa or from skin cells. There is then used a purification process of several steps, namely: disaggregation of the cells, elimination of the proteins by enzymatic digestion, isolation/extraction of the DNA, amplification by pulverization, if necessary, and preservation from altering factors.

The DNA thus prepared is in the form of a precipitate in alcohol.

The above protocol is well known and can be replaced by any other process, existing or new.

The DNA is then, according to the invention, placed in a sealed and corrosion-proof metallic capsule. Such so-called physical encapsulation is carried out in an atmosphere constituted by one or several inert gases such as rare gases and having a very low degree of humidity, preferably below 1 ppm of water, said atmosphere being at atmospheric pressure.

This is carried out for example with a conventional dry box.

Figure 1:
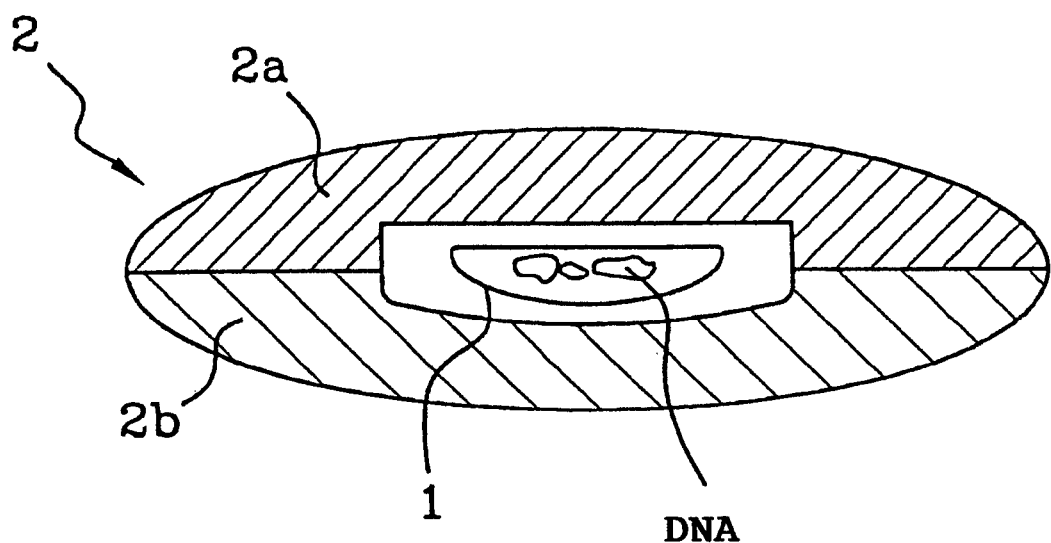
FIGS. 1 and 2 show containers encapsulating DNA.

The capsule, shown schematically at 1 in FIG. 1 of the accompanying drawing, is for example a gold capsule formed as a small circular pan closed by a lid press fitted about the periphery of the pan.

The diameter of the gold capsule is for example of the order of 5 mm and its thickness 2 to 3 mm.

The sealed assembly of the pan and its lid can be carried out by any suitable means.

Gold is preferable, because of its malleability and its non-oxidizing properties and property of non-contamination of the DNA. As a modification, a gold-based alloy or platinum could be used.

The atmosphere during encapsulation is dried so as to avoid hydrolysis and oxidation of the DNA after sealing.

The quantity of DNA placed in the capsule, for example about 30 micrograms, is largely sufficient to permit a substantial number of separate removals of DNA from the capsule in the course of its preservation.

Such a packaging can suffice to ensure the perpetual preservation of the genetic inheritance for tens or even hundreds of thousands of years, to the extent of course to which said capsule retains its integrity.

This packaging protects the DNA in particular as to:

chemical or enzymatic hydrolysis reactions;

cleavage induced by ultraviolet radiation or any ionizing radiation such as x-rays or gamma rays;

oxidation by the oxygen of the air.

Preferably, and to reinforce the preservation of the DNA, the capsule 1, namely said gold capsule, is itself enclosed in a sealed container 2 of a material having good mechanical properties, better to protect the capsule 1 relative to mechanical attack, in particular vibrations, shocks and crushing, or any other attack, for example a temperature increase and, generally speaking, so as to protect said capsule against the environment, whether normal or abnormal.

The container 2 can be a type of small box with two portions 2a, 2b, sealed or secured by any other means to ensure the integrity and the sealing of the assembly.

The container 2 can for example be of a suitable material, for example ceramic, composite, metallic or polymeric.

According to another embodiment of the process of the invention, the DNA suitably prepared is, before being emplaced in the capsule 1, subjected to a so-called chemical encapsulation.

To this end, the DNA is clad with a polymer or copolymer that is inert relative to the DNA, for reinforcement of the protection as to altering factors, the DNA molecules being sheltered in the pores of the (co)polymer.

The cladding material is selected such that it can be ultimately dissolved so as to be able to recover the DNA molecules.

Any (co)polymer can be used, except those that might be reactive with the DNA molecule, those which would prevent the redissolution of the DNA and those which require for such a redissolution an acid solvent, which is to say having a pH equal to or below about 4.

Such a chemical encapsulation can be carried by placing the suitably prepared DNA, for example a pellet of DNA obtained by precipitation, in an acrylic or polyacrylic acid solution in methyl alcohol.

For example, there is placed in solution 50 cm$^3$ of methyl alcohol, 1 g of acrylic or polyacrylic acid. The alcohol is slowly evaporated to obtain a viscous gel. A mass of DNA of about 1 mm$^3$ in suspension in alcoholic solution is disposed within this gel.

The assembly is dried at 50° C. to obtain a solid block containing the DNA, which is then placed in the capsule 1 according to the process described above, with the difference that it is no longer necessary to operate in a dry box, the neutral atmosphere being maintained.

Ultimately, and at any time, after opening the envelopes 1 and 2, the DNA can be disencapsulated by immersion for 1 hour in ethyl alcohol. There is again obtained a mass of molecules identical to that obtained by the process of purification.

According to another example using another (co)polymer, a solution of 1 g of methyl methacrylate or methyl polymethacrylate is dissolved in 50 cm$^3$ of dichloromethane. The solvent is evaporated to obtain a viscous gel. A mass of about 1 mm$^3$ of DNA, in suspension in an alcoholic solution, is disposed within this gel. The assembly is dried at 50° C. to obtain a solid block containing the DNA, which is then placed in the capsule 1 under the same conditions as for the preceding example.

Ultimately, and at any time, after opening the envelopes 1 and 2, the initial DNA can be regenerated by dissolution of the (co)polymer in dichlorolomethane.

According to a modification of such chemical encapsulations, the (co)polymer is associated with organic molecules and/or inorganic salts for better protection relative to ultraviolet radiation and ionizing radiation. There can be particularly added to the (co)polymer ions of heavy metals to the extent however that there is no risk of injury to the DNA.

According to one example, there is dissolved 1 g of acrylamide or polyacrylamide in 25 cm$^3$ of distilled water. There is added to the solution 50 mg of copper acetate and 50 mg of zinc acetate. The water is slowly evaporated to obtain a viscous gel. A mass of about 1 mm$^3$ of DNA in suspension in an alcoholic solution is placed within this gel. The assembly is dried at 50° C. to obtain a solid block containing the DNA, which is then emplaced in the capsule 1 under the same conditions as the preceding examples.

It is to be noted that the chemical encapsulation within a (co)polymer has the advantage of producing a polymerization of individual balls, which renders more practical the ultimate removal of DNA, because it suffices to withdraw from the capsule one ball, without touching the others.

As a polymer usable according to the invention, there can also be cited agarose.

Finally, the invention is obviously not limited with the embodiments shown above but on the contrary covers all modifications, particularly as to the nature of the constituent materials of the capsules 1 or containers 2, the conditions of physical and chemical encapsulation, the nature of the (co)polymer for chemical encapsulation and its possible additives, as well as the shape and dimensions of said capsules 1 or containers 2.

Figure 2:
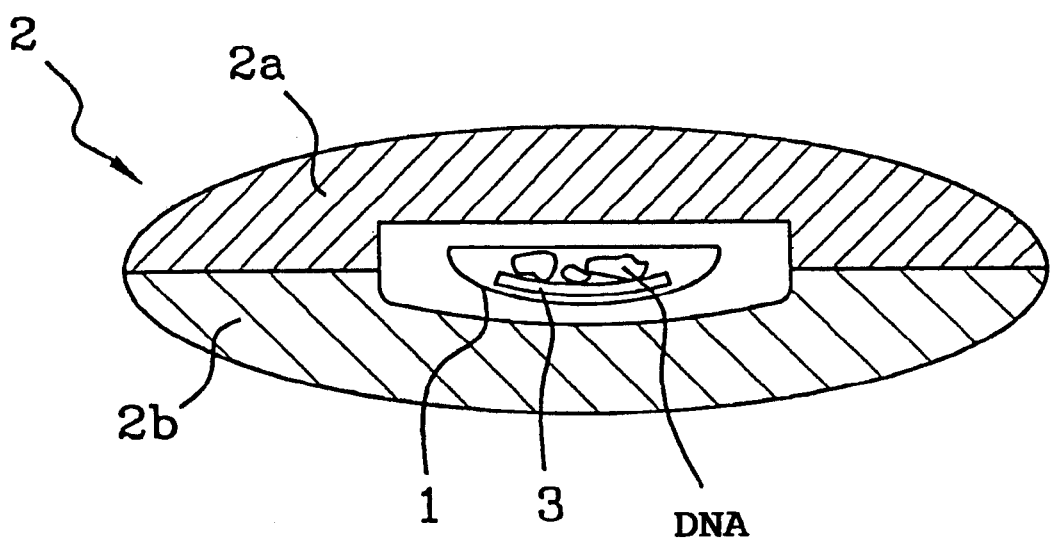

Thus as a modification, the DNA can be disposed on a glass dish, particularly a sodium calcium glass, as shown schematically at 3 in FIG. 2 of the accompanying drawing.

The DNA adheres to the glass of the dish 3, which can have, by way of example, a diameter of 7 mm and a height of 1.2 mm, said dish 3 being closed in a sealed manner in the capsule 1.

What is claimed is:

1. A process for the long term preservation of DNA molecules, comprising the steps of:

extracting and purifying the DNA; and carrying out an encapsulation of said DNA molecules in a sealed corrosion proof metallic capsule, said encapsulation being made under anoxic and dehumidified conditions.

2. The process according to claim 1, wherein said encapsulation is made in an atmosphere constituted by one or several inert gases and having a degree of humidity less than or equal to 1 ppm of water.

3. The process according to claim 1, wherein said encapsulation is made after submitting said DNA molecules to a chemical encapsulation by cladding with a (co)polymer.

4. The process according to claim 3, wherein said chemical encapsulation is carried out with a hybrid constituted of said (co)polymer, of organic and/or inorganic salt molecules, for increased protection of the DNA with respect to ultraviolet or ionizing radiations.

5. The process according to claim 4, wherein said hybrid is constituted of a (co)polymer and ions of heavy metal.

6. The process according to claim 3, wherein said (co)polymer is dissolved in a solvent, thereafter evaporated to obtain a viscous gel, then a predetermined mass of DNA in suspension in an alcohol solution is placed within said gel and the assembly is dried to obtain a solid block containing the DNA.

7. The process according to claim 6, wherein said chemical encapsulation is followed by an encapsulation in a sealed corrosion proof metallic capsule (1), in an atmosphere constituted by one or several inert gases.

8. The process according to claim 1, wherein said capsule (1) is disposed in a sealed container (2) resistant to shock and crushing.

9. The process according to claim 1, wherein before its encapsulation in the metallic capsule (1), the DNA is disposed in a glass dish.

10. A preservative packing obtained according to the process of claim 1, which is constituted of a capsule of malleable metal or metallic alloy and having corrosion-proof and non-contaminating properties as to the DNA, closed in a sealed manner by a lid.

11. The packaging according to claim 10, which is enclosed in a container (2) in a material selected from the group consisting of ceramics, composites, metals and polymers.

12. The packaging according to claim 10, which further comprises, within the metallic capsule (1), a glass dish (3) on which the DNA is disposed.

13. The packaging according to claim 12, wherein said dish (3) is constituted of a sodium-calcium glass.

* * * * *